United States Patent [19]

Willis et al.

[11] 4,033,330
[45] July 5, 1977

[54] TRANSCUTANEOUS pH MEASURING INSTRUMENT

[75] Inventors: Barry G. Willis, Palo Alto; Henry A. Schade, Jr., Mount View; Michael J. Farrell, Woodside, all of Calif.

[73] Assignee: Hewlett-Packard Company, Palo Alto, Calif.

[22] Filed: Sept. 8, 1975

[21] Appl. No.: 611,387

[52] U.S. Cl. .............................. 128/2 G; 128/2 L; 356/39; 356/42
[51] Int. Cl.² .................................. A61B 10/00
[58] Field of Search ........... 128/2 L, 2 E, 2 G, 2 A, 128/2.1 E; 356/39, 42

[56] References Cited

UNITED STATES PATENTS

| | | | |
|---|---|---|---|
| 3,461,856 | 8/1969 | Polanyi | 128/2 L |
| 3,578,865 | 5/1971 | Traver | 356/70 |
| 3,659,586 | 5/1972 | Johns et al. | 128/2 E |
| 3,793,525 | 2/1974 | Burch et al. | 250/343 |
| 3,795,239 | 3/1974 | Eberhard et al. | 128/2 E |
| 3,811,776 | 5/1974 | Blau, Jr. | 356/51 |
| 3,811,777 | 5/1974 | Chance | 128/2 L X |
| 3,825,342 | 7/1974 | Lubbers et al. | 128/2 L X |
| 3,878,107 | 4/1975 | Pembrook et al. | 250/343 |
| 3,918,434 | 11/1975 | Lubbers et al. | 128/2 E X |

Primary Examiner—Kyle L. Howell
Attorney, Agent, or Firm—Ronald E. Grubman

[57] ABSTRACT

A transcutaneous pH measuring device is provided in which a known volume of fluid is brought into equilibrium with body fluids through a membrane on a portion of skin whose surface layers have been stripped away. The fluid contains a pH sensitive dye. Optical measurements of the transmission characteristics of the fluid are obtained when the fluid is in the optical path. During portions of each operating cycle, the fluid is driven back into the vicinity of the skin to pH equilibrate with body fluids while standardization measurements are obtained using an optical plug of known transmission characteristics in the optical path.

7 Claims, 3 Drawing Figures

TRANSCUTANEOUS pH MEASURING INSTRUMENT

BACKGROUND AND SUMMARY OF THE INVENTION

In modern medical applications the use of transcutaneous measurement of blood parameters is becoming of increasing importance. Typically, the outermost layer of a small area of skin on a patient is removed, e.g., by repeated application of a strip of adhesive tape. A measuring device may then be sealed onto the stripped area of the skin so that the environment in the device can equilibrate with the environment of the body fluids at the surface of the skin. Measurements may then be made to determine parameters of interest such as blood pH or $CO_2$ concentration in the blood. One such device is described in co-pending U.S. patent application Ser. No. 547,670, titled "Medical-Analytical Gas Detector" by Paul E. Stoft et al., and assigned to the present assignee.

In some transcutaneous measuring devices known in the prior art body fluids are drawn into a chamber and brought into contact with a pH sensing glass electrode. With respect to transcutaneous measurements, pH electrodes of this kind are disadvantageous particularly in that problems with reference junction potentials may cause unstable response with time.

in accordance with the illustrated preferred embodiments, the present invention provides a transcutaneous pH measuring device in which a chamber containing a known volume of fluid is brought into equilibrium with body fluids through a membrane on a portion of skin whose surface layers have been stripped away. The volume of fluid contains a pH-sensitive dye whose optical transmission characteristics at different frequencies depends on the concentration of hydrogen ions in the fluid. The device includes a mechanism to draw the fluid into a chamber positioned between an optical source and an optical detector. When the fluid is in the chamber, optical measurements of its transmission characteristics at different frequencies are obtained. These measurements are then analyzed to provide an indication of the pH of the blood. During certain portions of each operating cycle, the fluid is driven out of the optical chamber and back into the vicinity of the skin by an optical plug of known transmission characteristics. While the fluid again comes into equilibrium with the blood, the optics of the system can be normalized by measurements through the optical plug.

DESCRIPTION OF THE PREFERRED EMBODIMENTS

Figure 1:
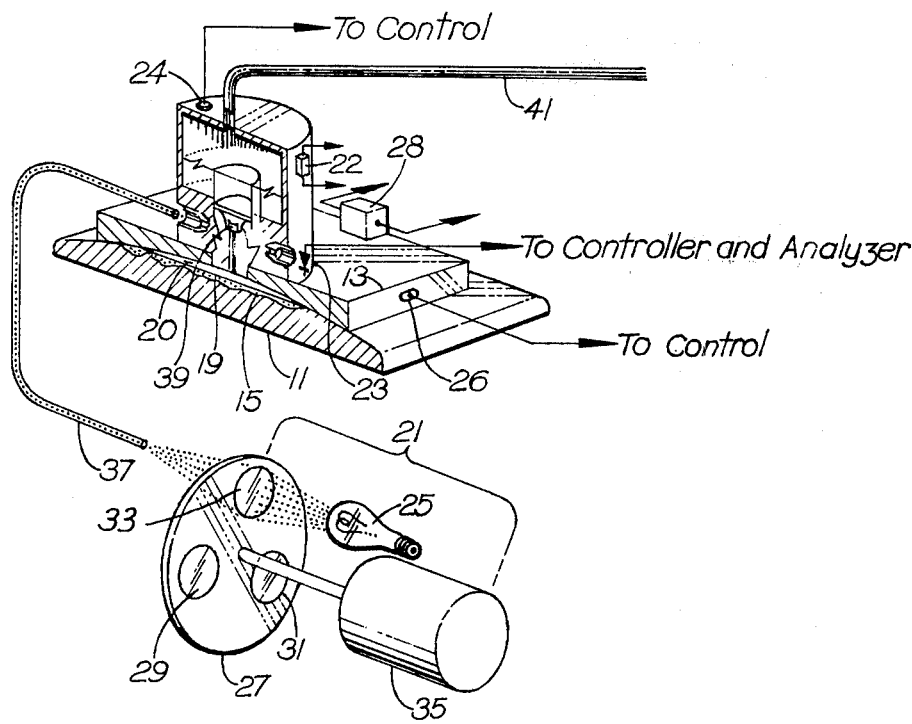
FIG. 1 is a schematic representation of a transcutaneous pH measuring device.

In FIG. 1 there is illustrated a section of skin 11 of a patient whose blood pH is to be measured. In accordance with procedures known to those skilled in the art, a small area of the outer layer of the skin may be scraped or otherwise removed. After the skin has been scraped, a sensor including a housing 13 is brought into contact with the exposed area. A membrane 15 which permits two-way migration of hydrogen ions defines a boundary between the scraped skin area and the housing. Membrane 15 may be, e.g., of cellulose acetate or Cuprophane or other suitable materials. A measuring chamber 17 internal to the housing is connected via a channel 19 to a dome-like region 20 above membrane 15.

Chamber 17 is located in the optical path between an optical source 21 and an optical detector 23. In this embodiment the optical source is illustrated as being a light source 25 positioned adjacent to a rotating wheel 27 containing optical filters 29, 31, and 33. When filter wheel 27 is rotated, e.g., by means of a motor 35, the different optical filters are sequentially presented in the path of the optical beam from source 25. Light of three different frequencies is thereby provided, to be carried by a light pipe 37 to illuminate chamber 17. Optical detector 23 may be any of a number of detectors known in the art which are sensitive to the frequencies employed (examples of which will be discussed in detail below).

Measuring chamber 17, channel 9 and dome-like volume 20 contain a measuring liquid whose optical transmission characteristics depend on the hydrogen ion concentration therein. For example, a saline solution of about the same salt concentration as the blood and containing a dye such as "phenol red" in a concentration of about $1 \times 10^{-4}$ m/l has been employed. As will be described in more detail below, the optical absorption characteristics of phenol red as a function of wave length are strongly dependent on the hydrogen ion content in the liquid. Since the measuring liquid is separated from the patient's blood by membrane 15, which permits free migration of hydrogen ions, the pH of the measuring liquid will equilibrate with the blood pH. Thus, by passing radiation of different frequencies through the measuring liquid and detecting the fraction of the radiation transmitted, an indication of the hydrogen ion content in the measuring liquid and hence of blood pH may be obtained.

To normalize the optics between readings, an optical plug 39 is periodically inserted into chamber 17. Optical measurements may then be obtained while radiation is transmitted through plug 39. In the schematic diagram of FIG. 1, a tube 41 represents a mechanism for driving optical plug 39 into chamber 17; for example, a pneumatic drive may be used. When the optical plug is forced down, the measuring liquid in chamber 17 is also forced down through column 19 into dome-like region 20 above membrane 15. Thus, while optical readings are taken through plug 39, the measuring liquid is again allowed to come into equilibrium with the body fluids at the surface of the skin. When optical plug 39 is withdrawn from chamber 17, measuring liquid is again drawn into the chamber and a new reading taken. Continuous monitoring of the blood is thereby provided.

In some practical embodiments of the invention it has proven advantageous to employ an electronic computer to control the cycling and also to perform analyses of the measurements. In FIG. 1, e.g., the output of detector 23 is indicated as being directed to a controller and analyzer which may consist of an A/D converter unit and associated logic controls under the control of an electronic computer. Numerous variations for control and analysis will be apparent to those skilled in the art.

Figure 2:
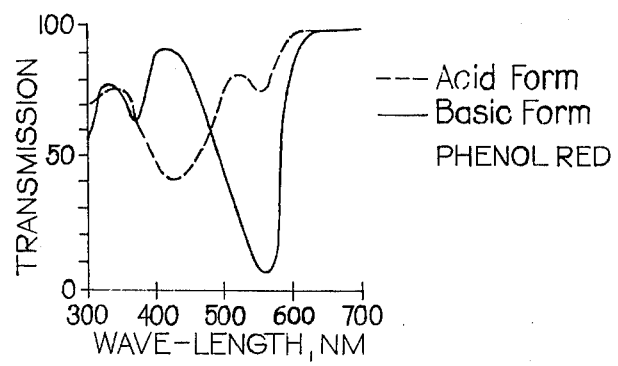
FIG. 2 is a graphical representation of the optical transmission characteristics for a preferred dye for use in pH measurement.

In FIG. 2, there is illustrated a graph of the transmission characteristics of the dye phenol red. The dye equilibrates in solution with hydrogen ions according to the equation $H_2$ Dye $\rightleftarrows$ $H^+$ + H Dye. $H_2$ Dye refers to the concentration of an acid form of the dye, while H Dye refers to the concentration of a basic form. From FIG. 2 it can be seen that the acid form has an absorption maximum at about 430 nanometers while the basic form has an absorption maximum at about 560 nanometers. By measuring the optical transmission at these two different wavelengths, the relative concentrations of the acid and basic forms of the dye in solution can be determined. From these determinations, the concentration of hydrogen ion in solution and hence the pH may be ascertained. A third reading is taken at a wavelength in the flat transmission regions of both forms of the dye (i.e., at about 650 nanometers) in order to obtain a measure of the optical quality of the solution. For example, if there are bubbles or particulates or other elements in solution, the measurement at this wavelength will serve to re-normalize the concentration measurements to account for these factors. For the purposes of this invention, the phenol red dye described above is particularly advantageous because each of the two forms of the dye exhibits an absorption maximum at a usable wavelength when the pH of the solution is in the vicinity of the pH expected in the blood (6.8 to 7.8). Other double-absorber dyes in the pH range expected in the blood would thus also be suitable for use according to the invention.

Referring back now to FIG. 1, measurements at the three wavelengths are first obtained while optical plug 39 is withdrawn from the optical path so that the measuring fluid is in the optical path. In order to render the measurement insensitive to variations in the remainder of the optics, optical plug 39 is driven down into chamber 17, thereby displacing fluid into the region 20 near the skin. Optical transmission is then remeasured through plug 39 at each of the three frequencies. These measurements may then be employed in a well known manner to normalize the measurements made on the dye in solution. If one cycle of operation is defined to mean a complete set of measurements made first with the liquid in chamber 17 and subsequently with optical plug 39 in chamber 17, then it has been found advantageous to maintain the plug in the chhamber for a relatively large portion of the cycle, e.g., about 80 percent. During this portion of the cycle, the measuring liquid is forced into volume 20 above diaphragm 15 and therefore comes into pH equilibrium with the blood.

It has been found that measurements obtained as described above may be sensitive to the temperature of the optical components and also to the temperature of the skin-instrument interface. It is therefore desirable to control these temperatures, e.g., by temperature sensing and heating. In FIG. 1 there is shown a heating element 22, e.g., a power transistor or electric heating coil, responsive to control circuitry (not shown) which maintains a desired temperature of the detector portion of the device. Heating element 22 is ultimately responsive to a temperature sensor 24, which may be, e.g., a thermistor. To regulate the temperature of the skin another sensor 26 and heating element 28 are positioned on housing 13 adjacent the skin.

From the above description, it may be seen that an advantage of the present invention in pH measurement is that the phenol red dye is in solution in the measuring liquid which is in pH equilibrium with the blood but does not contain the numerous heavy proteins present in the blood. Dyes generally, and phenol red particularly, are sensitive to those proteins so that measurements made with the dye in blood solution are disadvantageous. In the present invention, however, the dye in solution is maintained on one side of membrane 15 and the blood fluids on the other side. Although hydrogen ions are free to migrate through membrane 15 so as to pH equilibrate the two fluids, the larger proteins in the blood will not migrate across the diaphragm.

Figure 3:
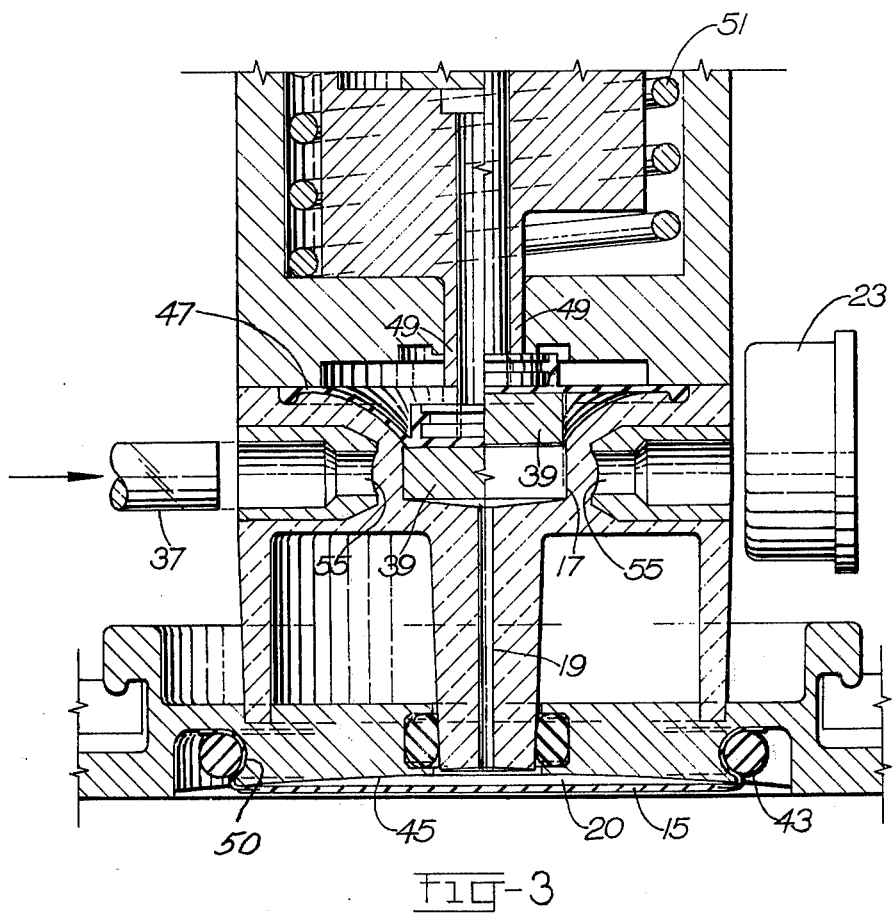
FIG. 3 shows a preferred embodiment of a pH measuring device in more detail.

In FIG. 3, there is again illustrated a membrane 15 positioned to come into contact with a scraped area of skin surface. Membrane 15 is stretched around a curved surface 50 and held in place by O-ring 43 which positions the membrane. A bottom surface 45 of the device is formed to create a dome-like volume between that surface and membrane 15. Measuring fluid in the volume may be maintained in contact with the skin surface through membrane 15. The fluid flows upward through a cylindrical connecting passage way 19 into a measuring chamber 17. In FIG. 3, two different operating modes of the invention are illustrated, one on the left side of the center line and the other on the right side of the center line. To the right of the center line is illustrated the condition of the device when liquid is present in measuring chamber 17. In this mode, an optical plug 39 (illustrated cross-hatched) is in a withdrawn position above chamber 17. Optical plug 39 may be fabricated, e.g., of glass or clear plastic. In a preferred embodiment of the invention, a diaphragm 47 is seated in the housing and positioned atop optical plug 39. The diaphragm is in grooved contact with a rod 49, which is responsive to variable forces tending to push the rod downward or return it to an upward position. For example, a hydraulic or pneumatic mechanism may be used to exert pressure to drive the rod downward while a spring may serve as a return mechanism. As shown in the right portion of the figure, rod 49 is in a withdrawn position so that diaphragm 47 is flat and not exerting force on optical plug 39. In this position the measuring fluid is in chamber 17. An optical beam is directed through chamber 17 to be detected by detector 23. For example, a light pipe 37 is illustrated as carrying an optical beam from an external source to be focused by a pair of lenses 53 and 55. In this position, the various wavelengths of light (described above in connection with FIGS. 1 and 2) pass through the measuring fluid in pH equilibrium with the blood.

Looking now at the portion of FIG. 3 to the left of the center line, rod 49 is pushed down somewhat, for example, by hydraulic pressure at the top of the piston. Diaphragm 47 is thereby extended and optical plug 39 is forced into chamber 17. Diaphragm 47 and optical plug 39 force measuring liquid out of chamber 17 down through passageway 19 into region 20 above membrane 15 in contact with the skin. During this portion of the cycle, optical measurements at all wavelengths are obtained through optical plug 39, thereby providing for standardization of the measurements with respect to variations in the optical components.

We claim:

1. A device for measuring the concentration of a substance in the blood, said device comprising:
   a housing;
   optical radiation source means mounted within said housing for providing optical radiation having at least one predetermined frequency component;

detector means mounted within said housing for detecting radiation at said at least one predetermined frequency;

a measuring chamber positioned within said housing in an optical path between said source means and said detector means;

means in the housing for maintaining a volumetric region adjacent an area of skin surface of the body when the device is brought into intimate contact with said area, said means allowing said substance in the blood to pass freely between the skin surface and said volumetric region while preventing the passage of undesired substances therebetween;

a measuring fluid in said volumetric region, said fluid having radiation absorption characteristics as a function of wavelength which vary as a function of the concentration of said substance in the blood; and means for drawing measuring fluid from said volumetric region into said measuring chamber and forcing measuring fluid from said measuring chamber into the volumetric region.

2. A device as in claim 1 further comprising:
standard means movably mounted in said housing for insertion into said measuring chamber when said measuring fluid is forced into said volumetric region, whereby said detector means is enabled to detect radiation passing through said standard means.

3. A device as in claim 2 wherein:
said measuring fluid comprises a plurality of components, each component having a radiation transmission spectrum including a transmission minimum at a separate wavelength; and
said detector means is adapted for detecting radiation at each of said separate wavelengths and at another common wavelength at which each of said components has a transmission maximum.

4. A device as in claim 3 wherein said measuring fluid comprises a solution of phenol red dye.

5. A device as in claim 2 wherein said measuring fluid comprises a solution of phenol red dye.

6. A device as in claim 1 wherein:
said measuring fluid comprises a plurality of components, each component having a radiation transmission spectrum including a transmission minimum at a separate wavelength; and
said dectector means is adapted for detecting radiation at each of said separate wavelengths and at another common wavelength at which each of said components has a transmission maximum.

7. A device as in claim 1 further comprising:
temperature sensing and control means for regulating temperatures in the vicinity of said housing.

* * * * *